United States Patent
Kogoi et al.

(10) Patent No.: US 6,335,002 B1
(45) Date of Patent: Jan. 1, 2002

(54) ULTRAFINE PARTICULATE ZINC OXIDE, PRODUCTION THEREOF AND COSMETIC MATERIAL USING THE SAME

(75) Inventors: Hisao Kogoi, Tokyo; Jun Tanaka, Toyama; Hayato Yamaya, Tokyo, all of (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/511,271

(22) Filed: Feb. 23, 2000

Related U.S. Application Data
(60) Provisional application No. 60/121,435, filed on Feb. 23, 1999.

(51) Int. Cl.$^7$ .......................... A61K 7/021; A61K 9/14; A61K 9/16
(52) U.S. Cl. .......................... 424/63; 424/489; 424/490
(58) Field of Search .................................. 424/489, 490, 424/63, 401; 106/481

(56) References Cited

U.S. PATENT DOCUMENTS
5,738,718 A * 4/1998 Mori et al. .................. 106/481

OTHER PUBLICATIONS

Patent Abstracts of Japan—abstract of JP–118133 (May 9, 1995).

Patent Abstracts of Japan—abstract of JP–7–025614 (Jan. 27, 1995).

Patent Abstracts of Japan—abstract of JP–6–144834 (May 24, 1994).

* cited by examiner

*Primary Examiner*—Thurman K. Page
*Assistant Examiner*—S. Howard
(74) *Attorney, Agent, or Firm*—Sughrue Mion, PLLC

(57) ABSTRACT

An ultrafine particulate zinc oxide where the ultrafine particulate zinc oxide has a specific surface area determined by the single-point BET technique of from about 10 to about 200 m$^2$/g and a substantially isotropic primary particle shape, wherein the specific volume determined by a tapping machine is from about 4 to about 40 ml/g, and additionally a process for producing the ultrafine particulate zinc oxide, a silica-coated ultrafine particulate zinc oxide powder and a cosmetic material using the zinc oxide powder.

18 Claims, 4 Drawing Sheets

ULTRAFINE PARTICULATE ZINC OXIDE, PRODUCTION THEREOF AND COSMETIC MATERIAL USING THE SAME

CROSS REFERENCE TO RELATED APPLICATIONS

This application is an application filed under 35 U.S.C. §111(a) claiming benefit pursuant to 35 U.S.C. §119(e)(i) of the filing date of Provisional Application 60/121,435 filed Feb. 23, 1999 pursuant to 35 U.S.C. §111(b).

FIELD OF THE INVENTION

The present invention relates to an ultrafine particulate zinc oxide which has a low coagulation of primary particles and coagulation can be reduced to such an extent that the particles can be very easily dispersed or suspended in an aqueous solvent even without passing through the process of grinding or after the slight dry grinding, and further which can be suitably used, for example, as a cosmetic powder and is favored with both transparency and ultraviolet-shielding ability. The present invention also relates to a production process of the ultrafine particulate zinc oxide.

BACKGROUND OF THE INVENTION

Many kinds of zinc oxide powders have been heretofore put on the market and applied to an extender blended in cosmetic materials and the like. Known production processes for these zinc oxide powders are roughly classified into a liquid phase process and a gas phase process. In the liquid phase process, zinc oxalate, zinc hydroxide or basic zinc carbonate is synthesized, precipitated, separated by filtration with rinse and then thermally decomposed to obtain zinc oxide. The powder obtained has a specific surface area of 50 $m^2/g$ or more. The liquid phase process is, however, disadvantageous in that the productivity is low because a batch system is fundamentally used; the fine particles obtained are in a solid-liquid mixed phase state and must be subjected to filtration and drying for finishing as a product. Accordingly, the production cost can be hardly reduced; and due to impurities remaining after the synthesis, higher purity cannot be attained. The gas phase process includes a French process of oxidizing zinc vapor and an American process of oxidizing zinc vapor generated at the smelting process of zinc ore. In this gas phase process, a zinc oxide powder having a specific surface area of 30 $m^2/g$ or more can be obtained. Other than these, various proposals for improved processes have been made in recent years with an attempt to further increase the specific surface area and improve the purity.

However, the zinc oxide powder produced by the above-described conventional processes has a problem in that the primary particles are not uniform in shape and particle size and are readily coagulated to form huge secondary particles. In the case of using such a zinc oxide powder in cosmetic materials or the like, it is necessary to unbind the coagulated particles by cracking or grinding. At this time, mixing of impurities due to abrasion during the cracking or grinding process inevitably takes place, as a result, not only the purity decreases but also the powder cannot be prevented from lack of uniformity in the shape of particles, the sharpness of the particle size distribution, and the mean particle size. Accordingly, when such a powder is used as a cosmetic material, the cosmetic material suffers from poor touch feeling. Furthermore, due to a large amount of grinding energy required, the cost increases.

SUMMARY OF THE INVENTION

An object of the present invention is to provide an ultrafine particulate zinc oxide which has a low coagulation of primary particles and in the case of application to a cosmetic material or the like, can be stably dispersed or suspended as extremely fine particles in an aqueous solvent without passing through any process for unbinding the coagulation, such as cracking or grinding, or after the slight dry grinding.

Another object of the present invention is to provide a production process of ultrafine particulate zinc oxide.

Still another object of the present invention is to provide a cosmetic material having both transparency and ultraviolet-shielding ability.

The present invention has been made under these circumstances and relates to an ultrafine particulate zinc oxide having a specific surface area determined by the single-point BET technique of from about 10 to about 200 $m^2/g$ and having a substantially isotropic primary particle shape, wherein the specific volume determined by a tapping machine is from about 4 to about 40 ml/g.

DETAILED DESCRIPTION OF THE INVENTION

Figure 1:
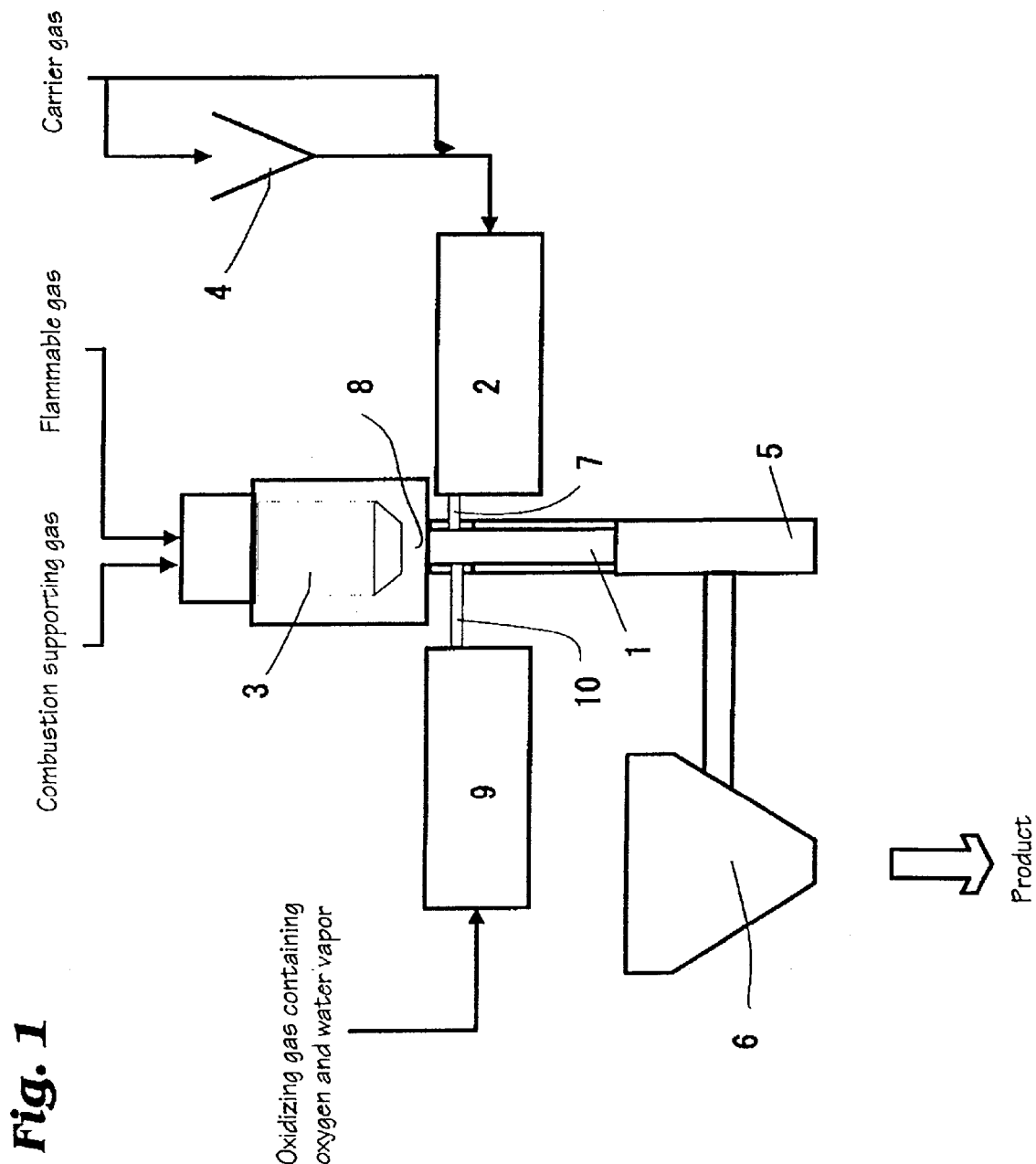
FIG. 1 is a schematic view showing one example of the reaction apparatus for use in the practice of the production process of the present invention.

The measurement method of the specific volume is described below.

A sample is previously dried at 105° C. to a constant weight and then passed through a 177 μm standard sieve. 3.0 g of the powder obtained is precisely weighed and gently placed in a 20 ml test tube with a measure. This test tube is mounted in a metal tube. The metal tube is covered and then dropped 400 times from the height of 45 mm at a rate of once per 2 seconds. Thereafter, the volume (ml) is read and V obtained by the expression: V=volume (ml)/3 (g) is defined as the specific volume of the sample.

As described above, zinc oxide powder conventionally assumes a huge secondary particle due to coagulation of primary particles and for unbinding the coagulation, the powder has heretofore been cracked or ground. This cracking or grinding process inevitably results in reduction of the purity and lack of uniformity in the shape of particles, the sharpness of the particle size distribution, and the mean particle size, and when the powder is applied to a cosmetic material or the like, the product suffers from poor touch feeling. According to the studies in more detail by the present inventors, the zinc oxide powder obtained above only has a specific volume as small as 3.5 ml/g or less. The present inventors have made extensive investigations on the specific volume of ultrafine particulate zinc oxide, which does not result in formation of huge secondary particles, with the proviso that a process responsible for lack of uniformity of the shape of particles, the sharpness of the particle size distribution, and the mean particle size, such as cracking or grinding, is fundamentally not performed. As a result, it has been found that an ultrafine particulate zinc oxide having a specific volume of from about 4 to about 40 ml/g obtained by the production process described later has a low coagulation to such an extent that the crushing process is not at all or scarcely necessary, therefore, can be immediately used as a raw material for cosmetic materials. The present invention has been accomplished based on this finding.

It has been also found that the above-described ultrafine particulate zinc oxide has a high whiteness and in turn a high ultraviolet-shielding ability and, moreover, has a high light transmittance in the visible light region and therefore high transparency. By virtue of these advantages, when the powder is used as a cosmetic material, extremely good properties can be imparted to the product.

The ultraviolet-shielding ability is described below. 20 g of polyglyceryl triisostearate (COSMOL-43, produced by The Nisshin Oil Mills, Ltd.), 200 mg of a powder (sample) dried at 105° C. to have a constant weight, 200 g of 1 mmφ $ZrO_2$ beads as a mixing medium, and 10 pieces of 10 mmφ $ZrO_2$ beads are charged into a vessel and mixed in a bench ball mill at 100 rpm for 30 minutes. The optical density of the mixture obtained is measured (corresponding to the reciprocal of the light transmittance) at respective wavelengths by a spectrophotometer for ultraviolet and visible region. The cell used is a 0.1 mm quartz cell and the wavelength of measurement is from 200 to 800 nm. Of course, blank correction of polyglyceryl triisostearate is performed. Among the values determined, the ratio of the optical density at a wavelength of 370 nm to the optical density at 530 nm is used as an index of the ultraviolet-shielding ability and the transparency (light transmittance in the visible light region).

In the case of conventional zinc oxide powders, the ratio of the optical density at a wavelength of 370 nm to the optical density at 530 nm is only on the order of from 1 to 3. On the other hand, in the ultrafine particulate zinc oxide of the present invention, the ratio of the optical density at a wavelength of 370 nm to the optical density at 530 nm is about 4 or more. Thus, it can be seen that the light transmittance in the visible light region is particularly excellent as compared with conventional powders.

The present invention provides a process for producing an ultrafine particulate zinc oxide having the above-described properties which conventional powders cannot possess, the process comprising oxidizing a zinc vapor in an atmosphere containing oxygen and water vapor, wherein a zinc vapor is jetted out from a first nozzle into a reactor together with an inert gas as a carrier gas, and an oxidizing gas containing oxygen and water vapor is jetted out from a second nozzle into the reactor, to cause oxidation reaction of zinc.

The present invention also provides a process for producing an ultrafine particulate zinc oxide having the above-described properties which conventional powders cannot possess, the process comprising oxidizing a zinc vapor in an atmosphere containing oxygen and water vapor, wherein a zinc vapor is jetted out from a first nozzle into a reactor together with an inert gas as a carrier gas, an oxidizing gas containing oxygen and water vapor is jetted out from a second nozzle into the reactor, and an oxidizing gas obtained by the combustion of a flammable gas such as propane or hydrogen with an excess combustion supporting gas such as oxygen or air is jetted out from a third nozzle into the reactor, to cause oxidation reaction of zinc.

As a result of extensive investigations on the production of the above-described ultrafine particulate zinc oxide having a high specific volume, it has been found that when zinc is oxidized by jetting out a raw material gas comprising a zinc vapor previously vaporized and an inert gas as the carrier gas from a first nozzle into a reactor, jetting out an oxidizing gas containing oxygen and water vapor from a second nozzle into the reactor, and/or jetting out an oxidizing gas obtained by the combustion of a flammable gas such as propane or hydrogen with an excess combustion supporting gas such as oxygen or air from a second or third nozzle, an ultrafine particulate zinc oxide having a low coagulation of primary particles and with a uniform shape and particle size can be produced.

The oxidizing gas containing oxygen and water vapor may be an oxidizing gas obtained by the combustion of a flammable gas such as propane or hydrogen with an excess combustion supporting gas such as oxygen or air. Furthermore, a plurality of nozzles may be used for each jetting of the oxidizing gas and the raw material gas.

The temperature at the time of jetting out the zinc vapor from a first nozzle together with an inert gas as the carrier gas is from about 900 to about 1,800° C., preferably from about 1,000 to about 1,500° C.

The temperature at the time of jetting out the oxidizing gas containing oxygen and water vapor from a second or third nozzle is from about 900 to about 1,200° C., preferably from about 1,000 to about 1,200° C.

In the stream conveying the oxidizing gas containing oxygen and water vapor jetted out from a second or third nozzle, the oxygen concentration is from about 5 to about 100 vol %, preferably from about 50 to about 100 vol %. The total of the oxygen concentration and the water vapor concentration in this stream is from about 5 to about 100 vol %.

At the time of jetting out the zinc vapor from a first nozzle together with an inert gas as the carrier gas, the jet velocity is from about 10 to about 200 m/sec, preferably from about 15 to about 100 m/sec.

In jetting out the oxidizing gas containing oxygen and water vapor from a second or third nozzle, the jet velocity is preferably from about 2 to about 250 m/sec.

After the oxidation reaction of zinc, the temperature is preferably controlled to a range where condensation of water does not occur. The temperature where condensation of water does not occur is about 100° C. or more, preferably from about 100 to about 150° C.

On taking notice of the V/A value obtained from a specific volume V and a specific surface area A of the ultrafine particulate zinc oxide produced by the above-described production process, it has been found that in conventional zinc oxide powder, this value is small and is 0.15 or less, but in the present invention, the V/A value is very large and is about 0.18 or more.

Furthermore, the ultrafine particulate zinc oxide produced by the above-described production process has a tendency to exhibit a unique property such that the V/A value lies in the range of from (Y value+200%) to (Y value−30%), the Y value being obtained by the following expression (1):

$$Y = V/A = -0.152 \operatorname{Ln}(A) + 0.745 \quad (1)$$

(wherein Ln(A) represents a natural logarithm of the specific surface area (unit: m$^2$/g)).

The production process of the present invention is described below by referring to the drawings attached hereto.

FIG. 1 is a schematic view showing one example of an apparatus suitably used for the production of ultrafine particulate zinc oxide of the present invention. In FIG. 1, the raw material zinc fed into a hopper 4 is transferred to a zinc vaporizer 2 by a carrier gas, and the zinc vapor generated in the zinc vaporizer 2 is introduced by an inert gas into a reactor 1 through a first nozzle 7.

Figure 2A:
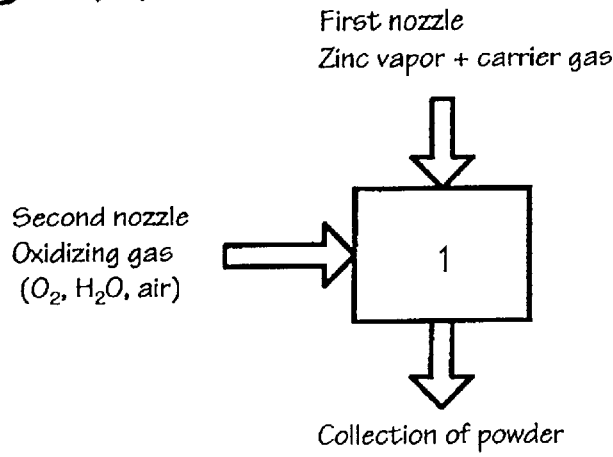
FIGS. 2(a)–2(c) are each a conceptual view showing the reaction apparatus for use in the production process of the present invention.
Figure 2B:
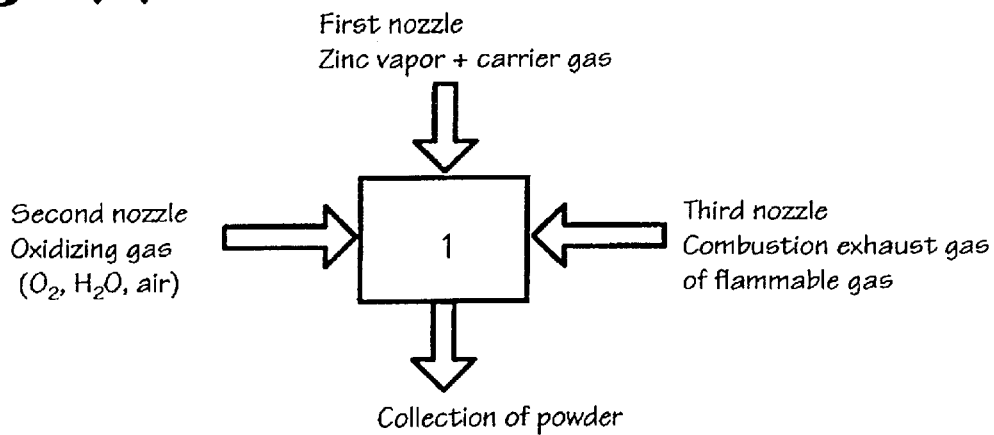
Figure 2C:
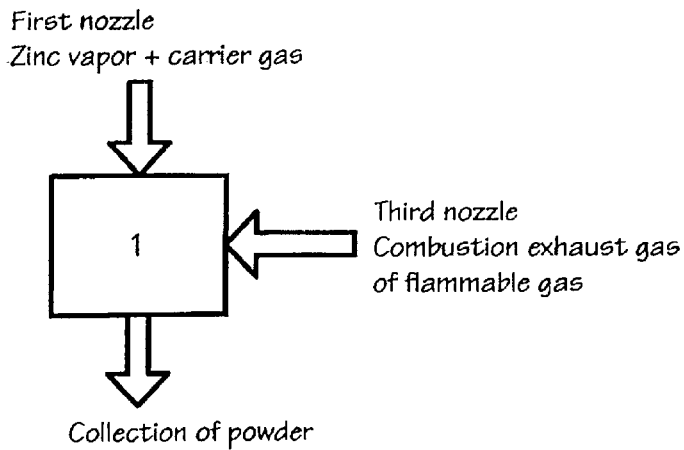

On the other hand, an oxidizing gas containing oxygen and water vapor is introduced into the gas heater 9, and the heated gas is introduced into the reactor 1 through a second nozzle 10 and/or an oxidizing gas obtained by the combustion of a flammable gas such as propane or hydrogen with an excess combustion supporting gas such as oxygen or air occurred in a combustion chamber 3 is introduced into the reactor 1 through a third nozzle 8, whereby zinc is oxidized (see, for example, FIGS. 2(a) to 2(c)).

This reaction is stopped by a cooling process where cooling air is blown into the zinc oxide transferred to a cooler 5 and thereby the reaction is stopped.

The shape of the particles, the sharpness of the particle size distribution and the mean particle size can be controlled by varying the length of the reaction field, the residence time or the like. Thereafter, zinc oxide is collected by a collecting means 6 (unit) such as a bag filter or cyclone, and used as a product.

In the present invention, the method for forming a coating of the silica-coated ultrafine particulate zinc oxide powder is not particularly limited and the method described, for example, in WO98/47476 may be used. However, the silica coating can be fundamentally formed by dipping the ultrafine particulate zinc oxide powder in a composition for forming a silica coating and keeping it at a predetermined temperature to selectively deposit silica on the surface of the zinc oxide powder. A method of previously preparing a composition for forming a coating and charging the zinc oxide powder thereinto to form a silica coating, or a method of previously suspending the zinc oxide powder in a solvent and adding thereto other raw material components to make a composition for forming a coating and thereby form a silica coating, may also be used. In other words, the order in charging the raw materials of the composition for forming a coating and the ultrafine particulate zinc oxide powder is not particularly limited and the coating can be formed whichever is charged earlier.

The ultrafine particulate zinc oxide powder and the silica-coated ultrafine particulate zinc oxide powder of the present invention may be employed over a wide range of products other than the cosmetic materials, for example, to pigments, ultraviolet-shielding materials and photocatalysts with controlled activity.

The cosmetic material of the present invention contains the ultrafine particulate zinc oxide powder and/or silica-coated ultrafine particulate zinc oxide powder and may be produced by a conventional production process additionally using commonly used raw materials which can be blended in cosmetic materials. The cosmetic material of the present invention contains from about 1 to about 40 mass % of ultrafine particulate zinc oxide powder or from about 1 to about 40 mass % of silica-coated ultrafine particulate zinc oxide powder. On considering the ultraviolet-shielding effect, the content of the ultrafine particulate zinc oxide powder and/or silica-coated ultrafine particulate zinc oxide powder is preferably from about 3 to about 25 mass %, more preferably from about 5 to about 20 mass %.

If the content of the ultrafine particulate zinc oxide powder and/or silica-coated ultrafine particulate zinc oxide powder is less than about 1 mass %, a sufficiently high ultraviolet-shielding effect may not be obtained, whereas if it exceeds about 40 mass %, a formulation may not be formed.

The cosmetic material of the present invention is not particularly limited as long as it contains the powder, and includes those obtained by dispersing the powder in a solvent or a solution. Examples of cosmetic material containing the powder include cosmetic materials in the form of powder, press, stick or liquid. Specific examples thereof include face powder, foundation, cosmetic powder, cheek color product, eye shadow, lipstick, eyeliner, mascara and eyebrow product. Specific examples of cosmetic material obtained by dispersing the powder in a solvent or a solution include cream, essence, lotion, skin lotion, milky lotion and mousse. In particular, the ultrafine particulate zinc oxide powder and/or silica-coated ultrafine particulate zinc oxide powder of the present invention is preferably used for solid powder cosmetics.

The present invention is described in greater detail below by referring to the Examples and Comparative Examples, however, the present invention should not be construed as being limited to these Examples. Unless otherwise indicated, all parts, percents, ratios and the like are by weight.

Evaluation Method of Physical Properties

The physical properties were measured and evaluated using the following methods.

For the X-ray diffraction, an apparatus, Model 2000/PC, manufactured by Rigaku KK was used.

The specific surface area was measured in the conditions for the single-point BET technique using a Monosorb-type apparatus manufactured by Quantachrome.

The specific volume was measured by the method according to the Standards for Cosmetic Ingredients using a tapping machine manufactured by Kuramochi Kagaku Kiki Seisakusho.

For the initial evaluation of transparency of the zinc oxide (sample), 200 mg of a sample was suspended in 20 g of polyglyceryl triisostearate (COSMOL-43, produced by The Nisshin Oil Mills, Ltd.) using a bench ball mill V-1M manufactured by Irie Seisakusho and determined by light transmittance at a wavelength of from 280 to 700 nm by a predetermined method using an spectrophotometer for the ultraviolet and visible region, UV-160 manufactured by Shimadzu Corporation.

EXAMPLE 1

An ultrafine particulate zinc oxide was produced using the reaction apparatus shown in FIG. 1 (the same applies to the following Examples 2 to 4).

A container having a large heat transfer surface area such that zinc vaporizes in an amount of 9 kg/hr was heated up to 1,150° C., then nitrogen as the carrier gas was blown into the container at 4 $Nm^3$/hr, and the vapor generated was introduced into a reaction tube from a nozzle 7 under thermal insulation. On the other hand, air and water at a flow rate of 20 $Nm^3$/hr and 700 ml/hr, respectively, were heated at 1,100° C., introduced into the reaction tube from a nozzle 10 and reacted with the above-described raw material gas. The X-ray diffraction of the white powder obtained was examined and the powder was found to be Zincite, thus, the powder was identified as zinc oxide. The more particular production conditions are shown in Table 1.

The physical properties of the thus-obtained ultrafine particulate zinc oxide (Example Material 1) are shown in Table 2.

EXAMPLE 2

A container having a large heat transfer surface area such that zinc vaporizes in an amount of 4 kg/hr was heated up to 1,100° C., then nitrogen as the carrier gas was blown into the container at 1 $Nm^3$/hr, and the vapor generated was introduced into a reaction tube from a nozzle 7 under thermal insulation. On the other hand, oxygen and water at a flow rate of 40 $Nm^3$/hr and 6 l/hr, respectively, were heated at 1,100° C., introduced into the reaction tube from a nozzle 10 and reacted with the above-described raw material gas. The X-ray diffraction of the white powder obtained was examined and the powder was found to be Zincite, thus, the powder was identified as zinc oxide. The more particular production conditions are shown in Table 1.

The physical properties of the thus-obtained ultrafine particulate zinc oxide (Example Material 2) are shown in Table 2.

EXAMPLE 3

A container having a large heat transfer surface area such that zinc vaporizes in an amount of 10 kg/hr was heated up to 1,100° C., then nitrogen as the carrier gas was blown into the container at 2 $Nm^3$/hr, and the vapor generated was introduced into a reaction tube from a nozzle 7 under thermal insulation. On the other hand, oxygen and water at a flow rate of 120 $Nm^3$/hr and 15 l/hr, respectively, were heated at 1,150° C., introduced into the reaction tube from a nozzle 10 and reacted with the above-described raw material gas. The X-ray diffraction of the white powder obtained was examined and the powder was found to be Zincite, thus, the powder was identified as zinc oxide. The more particular production conditions are shown in Table 1.

The physical properties of the thus-obtained ultrafine particulate zinc oxide (Example Material 3) are shown in Table 2.

EXAMPLE 4

A container having a large heat transfer surface area such that zinc vaporizes in an amount of 6 kg/hr was heated up to 1,150° C., then nitrogen as the carrier gas was blown into the container at 2 $Nm^3$/hr, and the vapor generated was introduced into a reaction tube from a nozzle 7 under thermal insulation. On the other hand, oxygen and water at a flow rate of 20 $Nm^3$/hr and 400 ml/hr, respectively, were heated at 1,150° C., introduced into the reaction tube from a nozzle 10 and reacted with the above-described raw material gas. The X-ray diffraction of the white powder obtained was examined and the powder was found to be Zincite, thus, the powder was identified as zinc oxide. The more particular production conditions are shown in Table 1.

The physical properties of the thus-obtained ultrafine particulate zinc oxide (Example Material 4) are shown in Table 2.

TABLE 1

| Production Condition | Example 1 | Example 2 | Example 3 | Example 4 |
|---|---|---|---|---|
| Temperature of raw material gas (° C.) | 1,150 | 1,100 | 1,150 | 1,150 |
| Amount of Zn vaporized (kg/hr) | 9 | 4 | 10 | 6 |
| Amount of carrier gas fed ($Nm^3$/hr) | 4 | 1 | 2 | 2 |
| Zn concentration in raw material gas (vol %) | 44 | 58 | 63 | 51 |
| Flow rate of oxidizing gas, Air ($Nm^3$/hr) | 20 | 0 | 0 | 0 |
| Flow rate of oxidizing gas, $O_2$ ($Nm^3$/hr) | 0 | 40 | 120 | 20 |
| Amount of water vapor, $H_2O$ (g/hr) | 700 | 6,000 | 15,000 | 400 |
| Total flow rate of oxidizing gas ($Nm^3$/hr) | 21 | 47 | 139 | 20 |
| Temperature of oxidizing gas (° C.) | 1,100 | 1,100 | 1,150 | 1,150 |
| Total of $O_2$ Concentration and $H_2O$ concentration in oxidizing gas (%) | 24 | 100 | 100 | 100 |
| Flow rate of raw material gas jetted out from nozzle (m/s) | 33 | 11 | 100 | 19 |
| Flow rate of oxidizing gas jetted out from nozzle (m/s) | 23 | 53 | 160 | 24 |
| Oxygen excess (%) | 273 | 5,839 | 7,007 | 1,946 |
| Collection temperature (° C.) | 120 | 130 | 130 | 130 |

Definition of Oxygen Excess in the Table;

$$\frac{\text{Amount of Oxygen Gas in Oxidizing Gas}}{\text{Theoretical Amount of Oxygen Gas Necessary for Reaction}} \times 100$$

Definition of Oxygen Excess in the Table;

Amount of Oxygen Gas in Oxidizing Gas/Theoretical Amount of Oxygen Gas Necessary for Reaction×100

Comparative Materials 1 to 4

Four kinds of commercially available zinc oxide powders, namely, ZnO-350 produced by Sumitomo Osaka Cement Co., Ltd. (Comparative Material 1), FINEX-50 produced by Sakai Chemical Industry Co., Ltd. (Comparative Material 2), Z-COTE produced by sunSmart Inc. (Comparative Material 3) and USP-1 produced by Zinc Corporation of America (Comparative Material 4), were selected and the physical properties thereof are shown in Table 2.

EXAMPLE 5

Production of Silica-Coated Ultrafine Particulate Zinc Oxide Powder:

In a 5 l-volume reactor, 991 ml of deionized water, 1,083 ml of ethanol (produced by Junsei Kagaku) and 6.7 ml of a 25 mass % aqueous ammonia (produced by Taisei Kako)

TABLE 2

Figure 3:
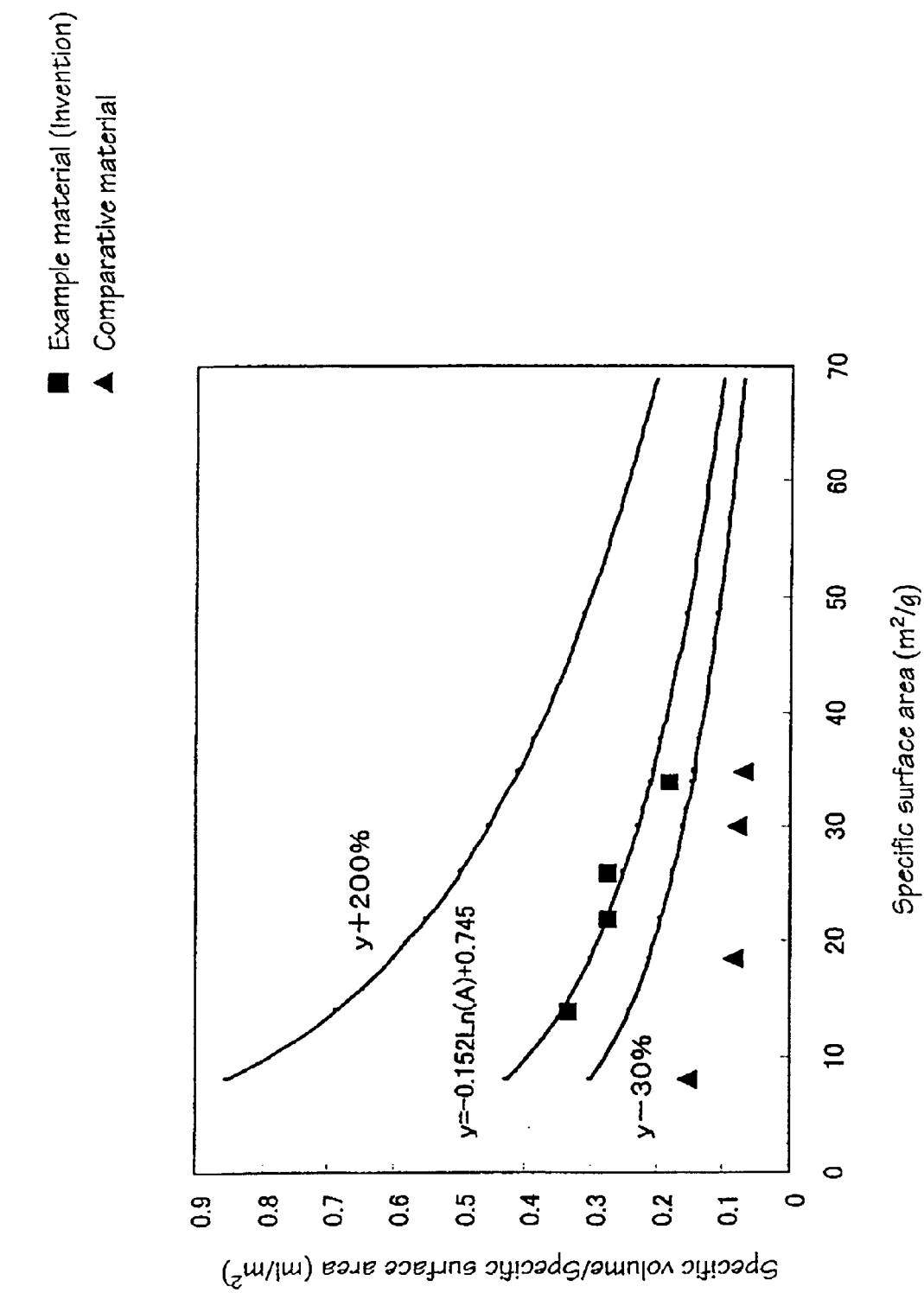
FIG. 3 is a graph showing the values of specific volume/specific surface area in Example Materials of the present invention and Comparative Materials (commercially available products)

|  | Example Material 1 | Example Material 2 | Example Material 3 | Example Material 4 | Comparative Material 1 | Comparative Material 2 | Comparative Material 3 | Comparative Material 4 |
| --- | --- | --- | --- | --- | --- | --- | --- | --- |
| Light transmittance | see FIG. 3 | see FIG. 3 | see FIG. 3 | see FIG. 3 | see FIG. 3 | see FIG. 3 | see FIG. 3 | see FIG. 3 |
| OD370 | 1.064 | 1.002 | 1.193 | 1.119 | 1.01 | 0.895 | 0.754 | 0.693 |
| OD530 | 0.263 | 0.239 | 0.246 | 0.338 | 0.397 | 0.24 | 0.416 | 0.402 |
| OD370/OD530 | 4.05 | 4.19 | 4.85 | 3.31 | 2.54 | 3.73 | 1.81 | 1.72 |
| Primary particle size (nm) | 48 | 44 | 31 | 76 | 35 | 30 | 57 | 130 |
| Mean particle size ($\mu$m) | 0.48 | 0.52 | 0.47 | 0.55 | 1.7 | 2.57 | 1.08 | 0.47 |
| Specific volume V (ml/g) | 6 | 7.1 | 6.1 | 4.65 | 2.35 | 2.5 | 1.55 | 1.23 |
| Specific surface area A ($m^2$/g) | 22 | 24 | 34 | 14 | 30 | 34.8 | 18.6 | 8.1 |
| V/A (ml/$m^2$) | 0.27 | 0.30 | 0.18 | 0.33 | 0.08 | 0.07 | 0.08 | 0.15 |
| L value by Hunter color tester | 94.2 | 93.8 | 93.5 | 94.6 |  |  |  |  |

Evaluation of Physical Properties

As apparent from Table 2, Example Materials 1 to 4 of the present invention were an ultrafine particulate zinc oxide powder having a large specific volume and a small bulk specific gravity. Furthermore, Example Materials 1 to 4 of the present invention all were an ultrafine particulate zinc oxide having a value of specific volume V/specific surface area A of 0.18 or more and the values were very large as compared with Comparative Materials 1 to 4 which are commercially available zinc oxide powders (see, FIG. 3). The tendency in the physical properties was analyzed by plotting the V/A values with respect to the specific surface area, then, it was surprisingly found that the group of Example Materials 1 to 4 of the present invention and the group of Comparative Materials 1 to 4 are present in the vicinity of respective peculiar asymptotic curves. Example Materials 1 to 4 of the present invention are present in the range of from +200% to −30% of the curve value (V/A) obtained according to the expression V/A=−0.152Ln(A)+ 0.745 (wherein Ln(A) represents a natural logarithm of a specific surface area). This tendency is unique as compared with the characteristic behavior (curve), of Comparative Materials.

Figure 4:
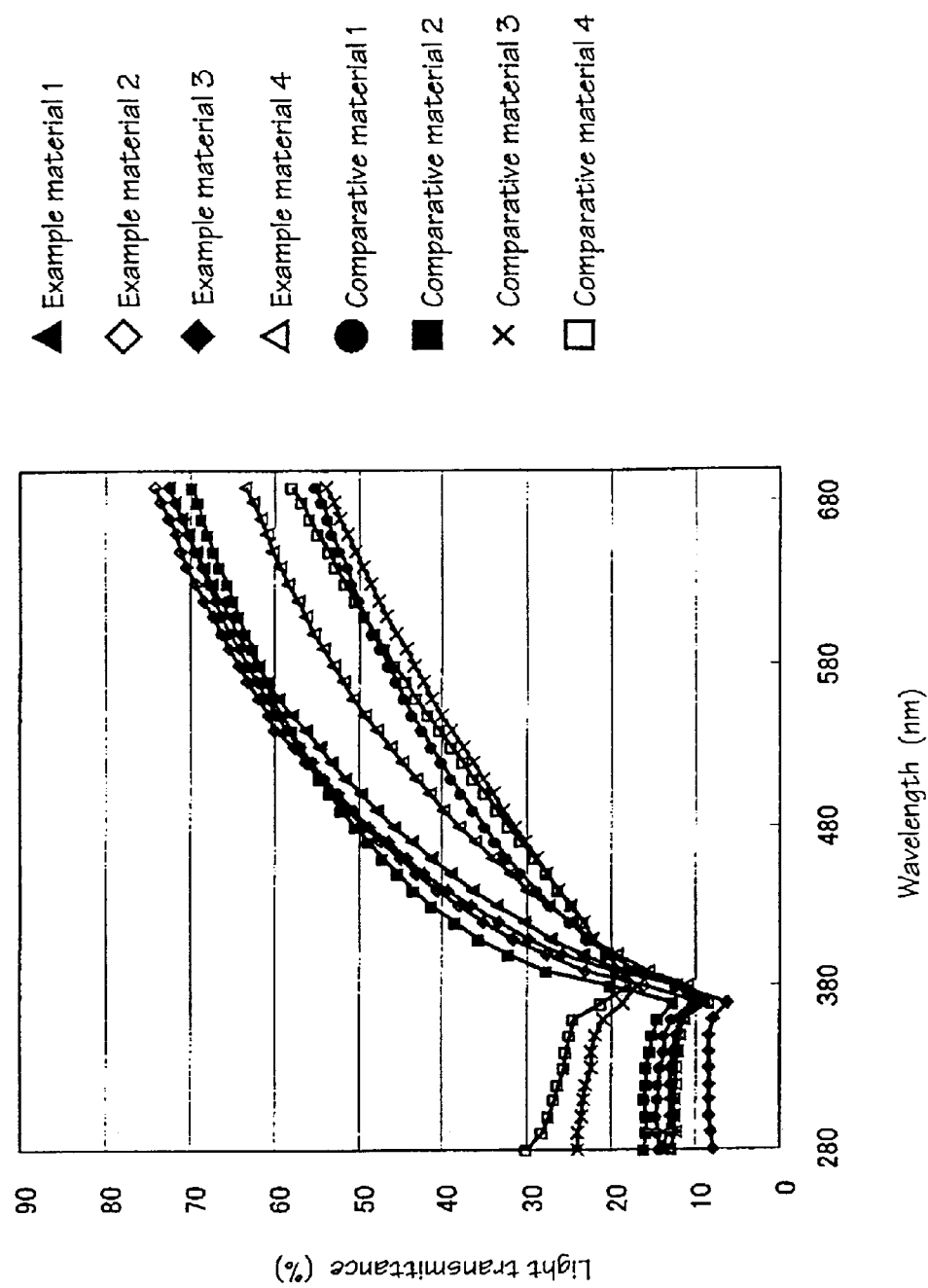
FIG. 4 is a graph showing the light transmittance in Example Materials of the present invention and Comparative Materials (commercially available products).

Furthermore, when an ultraviolet and visible light absorption spectrum of the dispersion system was measured, Example Materials 1 to 4 showed unique transparency as compared with Comparative Materials 1 to 4 (see, FIG. 4). In particular, Example Materials 1 to 4 were unique in that the ratio of the optical density at the wavelength of 370 nm (OD370) to the optical density at the wavelength of 530 nm (OD530) was 4 or more. Example Materials 1 to 4 were also unique with respect to the L value determined by a Hunter color tester.

The coating of silica on the ultrafine particulate zinc oxide powder and the formulation of a foundation using this silica-coated zinc oxide powder are described in the following Examples.

were mixed, and therein 67 g of zinc oxide powder (MZ0350 produced by Sumitomo Osaka Cement; primary particle size: 37 nm) was dispersed to prepare a suspension. Separately, 135 ml of tetraethoxysilane (produced by Nakarai Tesc) and 60 ml of ethanol were mixed to prepare a solution.

To the suspension under stirring with a stirrer, the solution prepared was added at a constant rate over 8.5 hours. The resulting mixed solution was ripened for 12 hours. The formation and ripening of the silica coating were performed at a pH of 10.5 and 35° C. Thereafter, the solid contents were separated by centrifugal filtration and vacuum dried at 50° C. for 12 hours to obtain silica-coated ultrafine particulate zinc oxide powder.

EXAMPLE 6

Foundation

A foundation having the following formulation was produced by a conventional method. As the silica-coated ultrafine particulate metal oxide powder, the silica-coated ultrafine particulate metal oxide powder obtained in Example 5 was used.

| Formulation of Foundation | |
| --- | --- |
| Fine particulate titanium oxide | 10.0 mass % |
| Silica-coated ultrafine particulate zinc oxide powder | 15.0 mass % |
| Mica | 20.0 mass % |
| Talc | 10.0 mass % |
| Zinc white | 5.0 mass % |
| Iron oxide (red) | optimum |
| Iron oxide (yellow) | optimum |
| Glycerin | 10.0 mass % |
| Purified water | 30.0 mass % |
| Perfume | optimum |

As described in the foregoing pages, the ultrafine particulate zinc oxide of the present invention has a low coagulation of primary particles and can be very easily dispersed or suspended in an aqueous solvent even without passing through the process of grinding or after the slight dry grinding, therefore, this ultrafine particulate zinc oxide can be suitably used, for example, for cosmetic materials and in this case, can impart transparency and ultraviolet-shielding ability to the cosmetic material.

The production process of ultrafine particulate zinc oxide of the present invention has a very high practical value because ultrafine particulate zinc oxide having the above-described action effects can be continuously produced without using specific facilities or chemicals.

While the invention has been described in detail and with reference to specific embodiments thereof, it will be apparent to one skilled in the art that various changes and modifications can be made therein without departing from the spirit and scope thereof.

What is claimed is:

1. An ultrafine particulate zinc oxide
   having a specific surface area determined by the single-point BET technique of from about 10 to about 200 $m^2/g$ and
   having a substantially isotropic primary particle shape,
   wherein the specific volume determined by a tapping machine is from about 4 to about 40 ml/g.

2. The ultrafine particulate zinc oxide as claimed in claim 1, wherein the V/A value obtained from a specific volume V and a specific surface area A is about 0.18 or more.

3. The ultrafine particulate zinc oxide as claimed in claim 2, wherein the specific surface area is from about 10 to about 70 $m^2/g$ and the V/A value obtained from a specific volume V and a specific surface area A is from (Y value+200%) to (Y value−30%), the Y value being determined by the following expression (1):

$$Y=V/A=-0.152Ln(A)+0.745 \quad (1)$$

wherein Ln(A) represents a natural logarithm of the specific surface area (unit: $m^2/g$).

4. The ultrafine particulate zinc oxide as claimed in any one of claims 1 to 3, wherein the ratio of optical density at a wavelength of 370 nm to optical density at a wavelength of 530 nm is about 4 or more, the optical density being determined by suspending the ultrafine particulate zinc oxide in polyglyceryl triisostearate.

5. The ultrafine particulate zinc oxide as claimed in any one of claims 1 to 3, wherein the L value indicated by a Hunter color tester is about 85 or more.

6. A process for producing an ultrafine particulate zinc oxide, comprising
   oxidizing zinc vapor in an atmosphere containing oxygen and water vapor by jetting zinc vapor from a first nozzle into a reactor together with an inert gas as a carrier gas, and jetting an oxidizing gas containing oxygen and water vapor from a second nozzle into the reactor, to cause oxidation reaction of zinc.

7. A process for producing an ultrafine particulate zinc oxide, comprising oxidizing zinc vapor in an atmosphere containing oxygen and water vapor by jetting zinc vapor from a first nozzle into a reactor together with an inert gas as a carrier gas, jetting an oxidizing gas containing oxygen and water vapor from a second nozzle into the reactor, and an oxidizing gas containing oxygen and water vapor, obtained by combustion of a flammable gas with an excess combustion supporting gas jetted from a third nozzle into the reactor, to cause an oxidation reaction of zinc.

8. The process for producing an ultrafine particulate zinc oxide as claimed in claim 6 or 7, wherein the method comprises jetting the zinc vapor from the first nozzle together with an inert gas as a carrier gas at a temperature of from about 900 to about 1,200° C.

9. The process for producing an ultrafine particulate zinc oxide as claimed in claim 6 or 7, wherein the process comprises jetting the zinc vapor from the first nozzle together with an inert gas as a carrier gas at a jet velocity of from about 10 to about 200 m/sec.

10. The process for producing an ultrafine particulate zinc oxide as claimed in claim 6 or 7, wherein the oxidizing gas containing oxygen and water vapor is obtained by combustion of a flammable gas with an excess combustion supporting gas.

11. The process for producing an ultrafine particulate zinc oxide as claimed in claim 6 or 7, wherein the process comprises jetting the oxidizing gas containing oxygen and water vapor from the second or third nozzle at a temperature of from about 900 to about 1,800° C.

12. The process for producing an ultrafine particulate zinc oxide as claimed in claim 6 or 7, wherein the process comprises jetting the oxidizing gas containing oxygen and water vapor from the second or third nozzle at a jet velocity of from about 2 to about 250 m/sec.

13. The process for producing an ultrafine particulate zinc oxide as claimed in claim 6 or 7, wherein the oxygen concentration in the oxidizing gas containing oxygen and water vapor jetting from the second or third nozzle is from about 5 to about 100 vol % and the total of the oxygen concentration and the water vapor concentration is from about 5 to about 100 vol %.

14. The process for producing an ultrafine particulate zinc oxide as claimed in claim 6 or 7, wherein after the oxidation reaction of zinc, the process comprises controlling the temperature to a range free of condensation of water.

15. The process for producing an ultrafine particulate zinc oxide as claimed in claim 14, wherein the temperature free of condensation of water is about 100° C. or more.

16. The process for producing an ultrafine particulate zinc oxide as claimed in claim 6 or 7, wherein the process comprises jetting the oxidizing gas from a plurality of nozzles.

17. A cosmetic material comprising from about 1 to about 40 mass % of an ultrafine particulate zinc oxide as recited in any one of claims 1 to 3 and a cosmetic base.

18. The cosmetic material as recited in claim 17 wherein the ultrafine particulate zinc oxide powder is silica-coated and the zinc oxide powder is present in an amount of about 1 to about 40 mass %.

* * * * *